(12) United States Patent
Dasgupta et al.

(10) Patent No.: US 9,897,543 B2
(45) Date of Patent: Feb. 20, 2018

(54) HALF-FREQUENCY SPECTRAL SIGNATURES

(75) Inventors: Anjan Kr. Dasgupta, Kolkata (IN); Sarita Roy, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 0 days.

(21) Appl. No.: 14/364,574

(22) PCT Filed: Aug. 6, 2012

(86) PCT No.: PCT/IB2012/001499
§ 371 (c)(1),
(2), (4) Date: Jun. 11, 2014

(87) PCT Pub. No.: WO2013/144673
PCT Pub. Date: Oct. 3, 2013

(65) Prior Publication Data
US 2014/0377792 A1 Dec. 25, 2014

(30) Foreign Application Priority Data

Mar. 29, 2012 (IN) .............................. 351/KOL/2012

(51) Int. Cl.
*G01N 21/21* (2006.01)
*G01N 21/64* (2006.01)
(Continued)

(52) U.S. Cl.
CPC ......... *G01N 21/64* (2013.01); *G01N 15/1459* (2013.01); *G01N 21/21* (2013.01);
(Continued)

(58) Field of Classification Search
CPC ....... G01N 21/6445; G01N 2021/6419; G01N 2021/216; A61B 5/0071
See application file for complete search history.

(56) References Cited

U.S. PATENT DOCUMENTS 4,127,773 A * 11/1978 West ..................... B07C 5/3427
250/226
4,191,940 A * 3/1980 Polcyn ................. G01N 21/314
250/226
(Continued)

FOREIGN PATENT DOCUMENTS

WO    0106918 A1    2/2001
WO    2005064336 A1    7/2005
(Continued)

OTHER PUBLICATIONS

Wang, L. S., et al. "[A study of nonlinear fraction frequency fluorescence spectra for tryptophane]." Guang pu xue yu guang pu fen xi= Guang pu 22.4 (2002): 641-644.*

(Continued)

*Primary Examiner* — Tri Ton
*Assistant Examiner* — Jarreas C Underwood
(74) *Attorney, Agent, or Firm* — Maschoff Brennan

(57) ABSTRACT

A technique for determining whether or not a fluorescent material exhibits a directionally dependent property, such as anisotropy or chirality, involves illuminating the particle at its excitation wavelength to stimulate fluorescent emission at both a full-frequency (fundamental) wavelength and a half-frequency wavelength. The ratio of the full-frequency signal strength to the half-frequency signal strength provides an indication of the sample's directionally dependent property. This half-frequency spectral analysis can be used to sort anisotropic particles suspended in fluid flowing through a flow cytometer. For instance, the present technique may be used to separate racemic mixtures of chiral enantiomers of cells, pharmaceutical compounds, and other samples.

23 Claims, 10 Drawing Sheets

(51) Int. Cl.
*G01N 33/15* (2006.01)
*G01N 33/58* (2006.01)
*B01D 59/00* (2006.01)
*G01N 15/14* (2006.01)
*G01N 15/00* (2006.01)

(52) U.S. Cl.
CPC ..... *G01N 21/6445* (2013.01); *G01N 21/6486* (2013.01); *G01N 33/15* (2013.01); *G01N 33/582* (2013.01); *B01D 59/00* (2013.01); *G01N 2015/0038* (2013.01); *G01N 2015/149* (2013.01); *G01N 2201/0683* (2013.01)

(56) References Cited

U.S. PATENT DOCUMENTS

| | | | |
|---|---|---|---|
| 4,203,670 A * | 5/1980 | Bromberg | G01N 21/6445 356/318 |
| 4,451,149 A * | 5/1984 | Noeller | G01N 21/6445 250/458.1 |
| 4,468,726 A | 8/1984 | Daigle et al. | |
| 4,488,814 A * | 12/1984 | Johnson | G01N 21/11 250/576 |
| 4,541,438 A * | 9/1985 | Parker | A61B 5/0059 424/9.61 |
| 4,912,059 A | 3/1990 | Newman et al. | |
| 4,946,279 A | 8/1990 | Ohkubo | |
| 4,954,435 A * | 9/1990 | Krauth | G01N 21/17 356/320 |
| 5,128,419 A * | 7/1992 | Fong | C08F 8/30 525/329.4 |
| 5,168,326 A | 12/1992 | Tokieda et al. | |
| 5,477,327 A | 12/1995 | Bergman | |
| 5,556,663 A * | 9/1996 | Chang | C08J 3/248 427/387 |
| 5,593,854 A * | 1/1997 | Berndt | G01N 21/6408 422/82.07 |
| 5,621,528 A | 4/1997 | Rokos | |
| 5,776,782 A * | 7/1998 | Tsuji | G01N 21/6408 422/82.07 |
| 5,876,672 A | 3/1999 | Dandliker et al. | |
| 5,896,198 A | 4/1999 | Chou et al. | |
| 6,055,451 A * | 4/2000 | Bambot | A61B 5/0071 250/341.3 |
| 6,232,608 B1 * | 5/2001 | Giebeler | G01N 21/6452 250/458.1 |
| 6,265,151 B1 * | 7/2001 | Canter | G01N 21/6486 435/4 |
| 6,327,037 B1 | 12/2001 | Chou et al. | |
| 6,654,119 B1 * | 11/2003 | Gould | G01J 3/02 250/458.1 |
| 6,834,237 B2 * | 12/2004 | Noergaard | A61B 5/7267 702/19 |
| 6,975,899 B2 * | 12/2005 | Faupel | A61B 5/0071 600/407 |
| 7,263,871 B2 | 9/2007 | Selker et al. | |
| 7,510,283 B2 * | 3/2009 | Bille | A61B 3/1015 351/211 |
| 7,569,821 B2 | 8/2009 | Ohashi | |
| 7,576,856 B2 * | 8/2009 | DiFoggio | G01J 3/02 250/269.1 |
| 8,098,428 B2 * | 1/2012 | Kawai | G01N 21/19 356/364 |
| 8,152,302 B2 * | 4/2012 | Bille | A61B 5/0062 351/221 |
| 9,164,028 B2 * | 10/2015 | Oda | G01N 21/31 |
| 2004/0064053 A1 | 4/2004 | Chang et al. | |
| 2005/0227366 A1 | 10/2005 | Tobe et al. | |
| 2007/0076199 A1 * | 4/2007 | Ode | G01J 3/02 356/301 |
| 2007/0158193 A1 | 7/2007 | Burgi et al. | |
| 2007/0237679 A1 * | 10/2007 | Hegazi | G01N 21/6402 422/82.08 |
| 2009/0101843 A1 | 4/2009 | Henshaw et al. | |
| 2009/0208548 A1 | 8/2009 | Mason et al. | |
| 2009/0220452 A1 | 9/2009 | Botti | |
| 2010/0253934 A1 | 10/2010 | D' Ascenzi et al. | |
| 2012/0044488 A1 | 2/2012 | Senac | |
| 2014/0023993 A1 * | 1/2014 | Zeng | G02B 21/0052 433/215 |
| 2015/0018644 A1 * | 1/2015 | Gulati | G01N 21/359 600/316 |

FOREIGN PATENT DOCUMENTS

| | | |
|---|---|---|
| WO | 2007002182 A1 | 1/2007 |
| WO | WO-2010/060454 | 6/2010 |
| WO | WO-2011/135399 | 11/2011 |

OTHER PUBLICATIONS

Jiang, Zhiliang, Weien Yuan, and Hongcheng Pan. "Luminescence effect of silver nanoparticle in water phase." Spectrochimica Acta Part A: Molecular and Biomolecular Spectroscopy 61.11 (2005): 2488-2494.*

Lobenstine, Eric W., William C. Schaefer, and Douglas H. Turner. "Fluorescence detected circular dichroism of proteins with single fluorescent tryptophans." Journal of the American Chemical Society 103.16 (1981): 4936-4940.*

International Search Report for PCT/IB2012/001499 dated Dec. 11, 2012.

Edwards, B.S., et al., "High-throughput flow cytometry for drug discovery," Expert Opinion on Drug Discovery, vol. 2, Issue 5, pp. 685-696 (May 2007).

Spinrad, R.W., and Brown J., "Effects of asphericity on single-particle polarized light scattering," Applied Optics, vol. 32, Issue 30, pp. 6151-6158 (Oct. 20, 1993).

Williams, R. M., et al., "Multiphoton microscopy in biological research," Current Opinion in Chemical Biology, vol. 5, Issue 5, pp. 603-608 (Oct. 1, 2001).

"Chiral Columns," accessed at https://web.archive.org/web/20120106162457/http://www.chiraltech.com/col_overview.asp, accessed on May 18, 2016, 1 Page.

"Front-Face Detection for Highly-Concentrated, Opaque, or Solid Samples," accessed at https://web.archive.org/web/20061209023323/http://www.jobinyvon.com/usadivisions/Fluorescence/applications/F-03_Front-Face_Det.pdf, accessed on May 18, 2016, 1 Page.

Baev, A., et al., "A quantum chemical approach to the design of chiral negative index materials," Optics Express, vol. 15, Issue 9, pp. 5730-5741 (2007).

Castiglioni, E., and Albertini, P., "An integrating sphere to measure CD from difficult samples," vol. 12, Issue 4, pp. 291-294 (2000).

Conger, B.M., "Polarized Photoluminescence from Nematic and Chiral-Nematic Liquid Crystalline Films," Dissertation, University of Rochester, 219 Pages (1998).

Davies, N.M., et al., "Effect of the enantiomers of flurbiprofen, ibuprofen, and ketoprofen on intestinal permeability," Journal of Pharmaceutical Sciences, vol. 85, Issue 11, pp. 1170-1173 (Nov. 1996).

Eriksson, T., et al., "Clinical pharmacology of thalidomide," Eur J Clin Pharmacol, vol. 57, No. 5, pp. 365-376 (Aug. 2001).

Guo, X., et al., "Angular measurements of light scattered by turbid chiral media using linear Stokes polarimeter," J Biomed Opt., vol. 11, No. 4, pp. 041105-1-041105-10 (Jul.-Aug. 2006).

Hassey-Paradise, R., et al., "Dissymmetries in Fluorescence Excitation and Emission from Single Chiral Chirality Molecules,", vol. 21, pp. E265-E276 (2009).

Hazen, R.M., et al., "Chiral Selection," accessed at https://web.archive.org/web/20120801125212/https://hazen.ciw.edu/research/chiral, accessed on May 18, 2016, 4 Pages.

Hiratsuka, T., "Monitoring the Myosin ATPase Reaction Using a Sensitive Fluorescent Probe: Pyrene-Labeled ATP," Biophysical Journal, vol. 72, pp. 843-849 (Feb. 1997).

International Search Report and Written Opinion for International Application No. PCT/I62011/001409 dated Oct. 12, 2011.

(56) References Cited

OTHER PUBLICATIONS

Jeong, K-U., et al., "Origin of Self-Assembled Helical Supramolecular Structures in Achiral C6 Biphenyl Carboxylic Acid Compounds," Chemistry of Materials, vol. 18, No. 3, pp. 680-690 (Jan. 5, 2006).

Johansson, L.B.-Å., and Langhals, H., "Spectroscopic studies of fluorescent perylene dyes," Spectrochimica Acta Part A: Molecular Spectroscopy, vol. 47 A, No. 7, pp. 857-861 (1991).

Kimaru, I.W., et al., "Characterization of Chiral Interactions Using Fluorescence Anisotropy," Analytical Chemistry, vol. 78, No. 24, pp. 8485-8490 (Nov. 18, 2006).

Kitaev, V., "Chiral nanoscale building blocks—from understanding to applications," Journal of Materials Chemistry, vol. 18, Issue 40, pp. 4745-4749 (Aug. 18, 2008).

Kriech, M.A., and Conboy, J.C., "Label-Free Chiral Detection of Melittin Binding to a Membrane," Journal of the American Chemical Society, vol. 125, No. 5, pp. 1148-1149 (Jan. 11, 2003).

Krishnan, K.S., and Balaram, P., "Perturbation of Lipid Structures by Fluorescent Probes," FEBS Letters, vol. 60, No. 2, pp. 419-422 (Dec. 1975).

Krstio, V., et al., "Magneto-dynamics of chiral carbon nanotubes," Chemical Physics Letters, vol. 390, Issues 1-3, pp. 25-28 (May 21, 2004).

Lakowicz, J.R., "Fluorescence Anisotropy," Principles of Fluorescence Spectroscopy, 3rd Edition, pp. 353-382 (2006).

Lim, S-A., "Ethambutol-associated Optic Neuropathy," Ann Acad Med Singapore, vol. 35, No. 4, pp. 274-278 (Apr. 2006).

Lin, J., et al., "A Practical Enantioselective Fluorescent Sensor for Mandelic Acid," Journal of American Chemical Society, vol. 124, Issue 10, pp. 2088-2089 (Feb. 16, 2002).

Manhas, S., et al., "Mueller matrix approach for determination of optical rotation in chiral turbid media in backscattering geometry," Optics Express, vol. 14, Issue 1, pp. 190-202 (2006).

McCarroll, M.E., et al., "Fluorescence Anisotropy as a Measure of Chiral Recognition," Journal of American Chemical Society, vol. 123, No. 13, pp. 3173-3174 (Mar. 13, 2001).

Moreira, A.B., et al., "Direct determination of paracetamol in powdered pharmaceutical samples by fluorescence spectroscopy," Analytica Chimica Acta, vol. 539, Issues 1-2, pp. 257-261 (May 10, 2005).

Narayanswamy, P.K., "The Raman spectra of water, heavy water and ice," Proceedings of the Indian Academy of Sciences—Section A, vol. 27, No. 4, pp. 311-315 (Apr. 1948).

Nilsson, C., and Nilsson, S., "Nanoparticle-based pseudostationary phases in capillary electrochromatography," Electrophoresis, vol. 27, No. 1, pp. 76-83 (Jan. 2006).

O'Connell, M.J., et al., "Chiral selectivity in the charge-transfer bleaching of single-walled carbon-nanotube spectra," Nature Materials, vol. 4, pp. 412-418 (2005).

Pike, J.N., "Fluorescence of mixed powder samples: a six-flux theory," Applied Optics, vol. 20, Issue 7, pp. (1981) 1167-1173.

Roy, S., et al., "Nanoparticle induced conformational change in DNA and chirality of silver nanoclusters," J Nanosci Nanotechnol, vol. 10, No. 2, pp. 819-825 (Feb. 2010).

Sekhon, B.S., "Enantioseparation of Chiral Drugs—An Overview," International Journal of PharmTech Research, vol. 2, No. 2, pp. 1584-1594 (Apr.-Jun. 2010).

Shemer, G., et al., "Chirality of Silver Nanoparticles Synthesized on DNA," Journal of American Chemical Society, vol. 128, No. 34, pp. 11006-11007 (Aug. 9, 2006).

Sparks, W., et al., "Circular Polarization in Scattered Light as a Possible Biomarker," Journal of Quantitative Spectroscopy & Radiative Transfer, vol. 110, Issue 14-16, pp. 1771-1779 (2009).

Spivey, A., "Chemistry I (Organic): Stereochemistry Hybridisation and Molecular Shape: Enantiomers," accessed at https://web.archive.org/web/20061011021213/http://www.ch.ic.ac.uk/local/organic/tutorial/ACS2.pdf, accessed on May 18, 2016, 5 Pages.

Stine, K.J., et al., "Comparison of Enantiomeric and Racemic Monolayers of N-Stearoylserine Methyl Ester by Fluorescence Microscopy," Langmuir, vol. 9, No. 8, pp. 2112-2118 (Aug. 1993).

Sui, J., et al., "Expanding proteomics into the analysis of chiral drugs," Molecular BioSystems, vol. 5, Issue 6, pp. 603-608 (Apr. 28, 2009).

Szöllösi, G., et al., "Preparation of Pt nanoparticles in the presence of a chiral modifier and catalytic applications in chemoselective and asymmetric hydrogenations," Journal of Materials Chemistry, vol. 15, Issue 25, pp. 2464-2469 (May 12, 2005).

Torsi, L., et al., "A sensitivity-enhanced field-effect chiral sensor," Nature Materials, vol. 7, No. 5, pp. 412-417 (Apr. 28, 2008).

Toukoniitty, E., et al., "Catalyst selection and solvent effects in the enantioselective hydrogenation of 1-phenyl-1,2-propanedione," Studies in Surface Science and Catalysis, vol. 130, pp. 3363-3368 (2000).

Tran, C.D., and Oliveira, D., "Fluorescence determination of enantiomeric composition of pharmaceuticals via use of ionic liquid that serves as both solvent and chiral selector," Analytical Biochemistry, vol. 356, pp. 51-58 (Sep. 1, 2006).

Tsumatori, H., et al., "Observation of Chiral Aggregate Growth of Perylene Derivative in Opaque Solution by Circularly Polarized Luminescence," American Chemical Society, vol. 12, No. 10, pp. 2362-2365 (Apr. 21, 2010).

Viedma, C., "Chiral Symmetry Breaking During Crystallization: Complete Chiral Purity Induced by Nonlinear Autocatalysis and Recycling," Physical Review Letters, vol. 94, No. 6, pp. 065504-1-065504-4 (Feb. 18, 2005).

Wang, J.T., et al., "Accurate Formulation of Faraday, Magnetic Circular Dichroism (MCD) and Kerr Effect of Light in Ferroelectromagnet," Journal of Superconductivity and Novel Magnetism, vol. 23, Issue 6, pp. 1155-1160 (Aug. 2010).

Wei, A., "Calixarene-encapsulated nanoparticles: self-assembly into functional nanomaterials," Chem Commun (Camb), vol. 15, pp. 1581-1591 (Apr. 21, 2006).

Williams, A.A., et al., "Determination of Enantiomeric Compositions of Analytes Using Novel Fluorescent Chiral Molecular Micelles and Steady State Fluorescence Measurements," J Fluoresc, vol. 18, No. 2, pp. 285-296 (Mar. 2008).

* cited by examiner

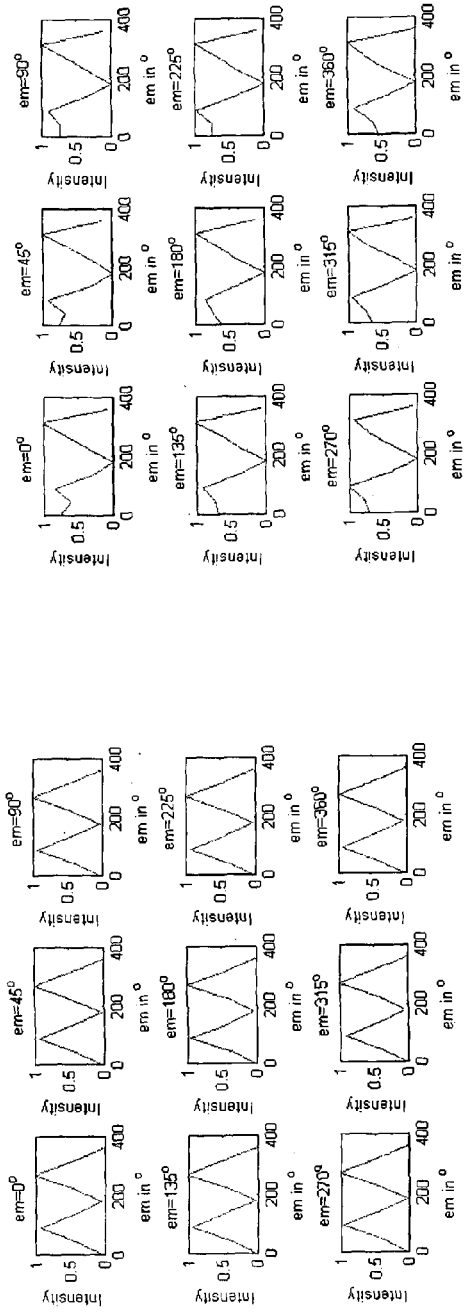
FIG. 5B
FIG. 5A
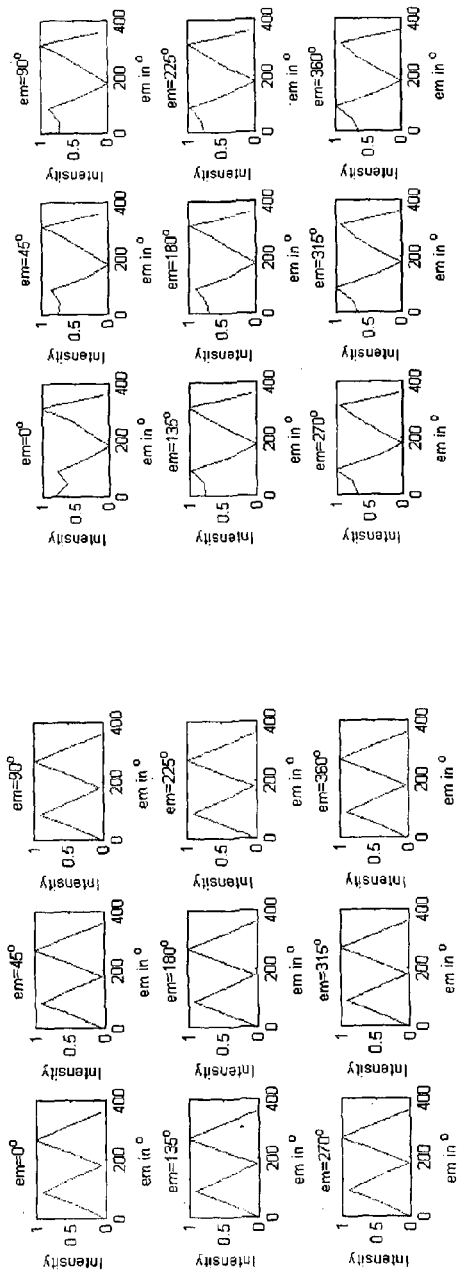
FIG. 6B
FIG. 6A

HALF-FREQUENCY SPECTRAL SIGNATURES

CROSS-REFERENCE TO RELATED APPLICATIONS

The present application claims priority to and the benefit as a national stage filing under 35 U.S.C. § 371 of International Application Serial No. PCT/IB2012/001499, filed on Aug. 6, 2012, which claims the priority of Indian Patent Application No. 351/KOL/2012, filed on Mar. 29, 2012. The entire contents of the foregoing applications are herein incorporated by reference.

BACKGROUND

Optical detection and analysis of small molecules, biomolecules, and cells can be broadly divided into two categories: absorption spectroscopy and emission spectroscopy. Absorption spectroscopy involves illuminating a sample with radiation over a range of wavelengths, such as over the visible and infrared portions of the electromagnetic spectrum, and measuring the intensity of the radiation transmitted through the sample. Subtracting the measured intensity from the intensity of the radiation incident on the sample gives the absorption spectrum, or amount of radiation absorbed by the sample as a function of frequency. In emission spectroscopy, incident radiation at a single wavelength causes the sample to fluoresce at one or more frequencies; the resulting plot of fluorescence intensity versus frequency is the sample's emission spectrum. Because each chemical compound has unique absorption and emission spectra, absorption and emission spectroscopy can be used to identify unknown samples.

Spectroscopic techniques can also be used to count, identify, and sort particles for purifying fluids and diagnosing disease. In flow cytometry, for example, particles are suspended in a fluid and passed through a beam of light. A detector senses the absorption or emission spectrum of the particles as they flow through the beam of light. High-throughput flow cytometry exploits a novel many-samples/one-file approach to dramatically speed data acquisition, to limit aspirated sample volume to as little as 2 µl/well, and to produce multi-sample data sets that facilitate automated analysis of samples in groups as well as individually. High-content multiparametric analysis capabilities have been exploited for assay multiplexing, allowing the assessment of biologic selectivity and specificity to be an integral component of primary screens. These and other advances in the last decade have contributed to the application of flow cytometry as a uniquely powerful tool for probing biologic and chemical diversity and complex systems biology.

Spectroscopic flow cytometry can be combined with polarimetric techniques to identify anisotropic and chiral particles, including different enantiomers of the same compound. As understood by those of skill in the art, an anisotropic particle has different dimensions along different axes—for example, an ellipsoid is anisotropic, whereas a sphere is isotropic. A chiral particle is a particle that lacks an internal plane of symmetry, i.e., a chiral molecule has a non-superimposable mirror image. Chiral particles are anisotropic, but anisotropic particles are not necessarily chiral.

The ability to distinguish anisotropic and chiral particles from isotropic particles is especially useful when sorting an active isomer from a detrimental or inactive isomer of a drug. In some cases, a Pockels cell or other device switches the polarization of the beam of light used to irradiate the particles in the flow cytometer between linearly polarized and circularly polarized states. Differences between the emission or absorption spectra for the different polarization states may indicate the presence of different isomers of the same compound in a given sample. Similarly, changes in the amount of scattered light and the direction in which the light is scattered as a function of polarization state may indicate the presence of particles with different shapes (e.g., isotropic versus anisotropic).

Recognizing the chirality of chemical and biological compounds is especially important for identifying different isomers of a single molecule and of chiral macromolecules, including proteins, DNA, and various metabolites. Chirality in nanotechnologies is also important in applications such as functional self assembly, enantioselective catalysis, separation, biosensing, and optical devices. There are many biological systems at microscopic and macroscopic levels which are enriched by chiral objects such as proteins, nucleic acids, carbohydrates, amino acids, and nucleotides.

SUMMARY

One embodiment of the present disclosure relates to methods of determining a nonlinear optical property of a fluorescent material, such as a fluorescent particle or non-fluorescent particle with a fluorescent tag. Exemplary nonlinear optical properties include both an anisotropy of or associated with the fluorescent material and a chirality of or associated with the fluorescent material. In at least one instance, the nonlinear optical property may be a unitless anisotropy value that ranges from 0.0 (isotropic) to 1.0 (anisotropic). A nonlinear optical property determined using the present techniques may be used to discriminate monomers and dimers.

An illustrative method begins with irradiation of the fluorescent particle at an excitation frequency (for example, at about 750 THz to about 30,000 THz), followed by detection of the fluorescent material's fluorescence spectrum. The fluorescence spectrum features a first peak at a first frequency (for example, at about 375 THz to about 750 THz) and a second peak at a second frequency equal to about half the first frequency. The next steps of the illustrative method include performing a comparison of the first peak to the second peak and determining whether the fluorescent material is chiral and/or anisotropic based on the comparison. In some embodiments, the fluorescent material includes a fluorescent particle, a cell with a fluorescent tag, a molecule with a fluorescent tag, or a pharmaceutical compound.

Irradiating the fluorescent material may include selecting radiation at the excitation frequency in a first polarization state, and detecting the fluorescence spectrum may include selecting the radiation emitted or scattered by the particle (i.e., radiation at the first and second frequencies) in a second polarization state. In some cases, the first polarization state is orthogonal to the second polarization state; in other cases, the first and second polarization states are the same. At least one of the first and second polarization states can be changed before detection of another fluorescence spectrum. Alternatively, or in addition, the fluorescent material may be irradiated at a first angle and the fluorescence spectrum may be detected at a second angle with respect to the fluorescent material. The first angle can be different than the second angle, for example, the first angle and the second angle can be 90° apart.

In one embodiment, detecting the fluorescence spectrum may include diffracting radiation emitted or scattered by the fluorescent material off a grating; filtering radiation at the excitation wavelength from the radiation emitted by the fluorescent material; and sensing the radiation emitted by the fluorescent material. Sensing the radiation emitted by the fluorescent material can include detecting the radiation at the first frequency and the second frequency at the same time (i.e., in parallel) or sequentially.

In certain embodiments, performing the comparison of the first peak to the second peak comprises estimating a first area under the first peak, estimating a second area under the second peak, and calculating a ratio of the first area to the second area. These areas may be estimated using a fluorometer. The ratio can be used to determine whether or not the fluorescent material is chiral and/or anisotropic. If the fluorescent material is chiral, the data may further be used to determine whether the fluorescent material has left-handed chirality or right-handed chirality. For instance, the handedness of chiral forms of a particular fluorescent material can be obtained by comparing the data to data for a reference compound which is a homologue of one or more of the chiral forms (i.e., a reference compound that has a similar structure to at least one of the chiral forms).

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and, together with the description, serve to explain principles of the disclosed technology.

FIGS. 5A and 5B are plots of full-frequency emission patterns for achiral pyrene and chiral L-tryptophan, respectively.

FIGS. 6A and 6B are plots of half-frequency emission patterns for achiral pyrene and chiral L-tryptophan, respectively.

DETAILED DESCRIPTION

Detection of optical emission(s) in the half-frequency domain enables discrimination between different particles, including monomers and dimers as well as different isomers of the same molecule, with higher classification potential than in the full-frequency domain. The present techniques are based on detecting photons at about half the frequency of the nominal fluorescence emission frequency of a sample. Half-frequency detection can be integrated with polarimetric analysis to enable new techniques for identifying, sorting, and separating anisotropic and chiral substances. For instance, the disclosed techniques may be used to identify different mirror-image stereoisomers, or enantiomers, of a single type of molecule.

In cell biology applications, the disclosed techniques may be used to identify normal and abnormal cell populations with a high level of discrimination. Half-frequency detection can also be used to enhance the population discriminatory power of flow cytometry by addition of multiple new dimensions in phase space (e.g., finer structural information provided by flow cytometry or fluorescence microscopy utilizing half frequency spectral signatures) representing the flow cytometric data. The present techniques may be useful in steady state spectrofluorometric techniques, time-resolved spectrofluorometric techniques, and correlation spectroscopy (or any imaging or flow cytometric detection principle based on correlation spectroscopy).

The present techniques may be applied in the biochemistry, analytical chemistry, pharmaceutical, and nanoparticles industries to name but a few applications. The present half-spectral signature techniques can be used not only for identifying anisotropy and chirality, or determining extent of chirality, also to separate out enantiomeric forms based on flow cytometry. For instance, the present techniques may be used to separate multi-walled carbon nanotubes from single-walled carbon nanotubes or other carbon nanotubes based on differences in anisotropy and chirality.

One important challenge in bioimaging is the search for appropriate fluorescent tags or probes for attaching to different compounds. If the same probe can be exploited beyond the domain of its conventional application by appropriate modulation (or modification) of the source and detector, the technology may be beneficial to end users. In some cases, half-frequency spectral signature technique may lead to the identification of new fluorescent tags and new uses for known fluorescent tags. For instance, each flurophore may have a specific intensity value at its full frequency and its half frequency. If two flurophores have identical emission wavelengths, they can still be discriminated using ratios of their half frequency and full frequency intensity values.

Instruments for Measuring Nonlinear Optical Properties

Figure 1A:
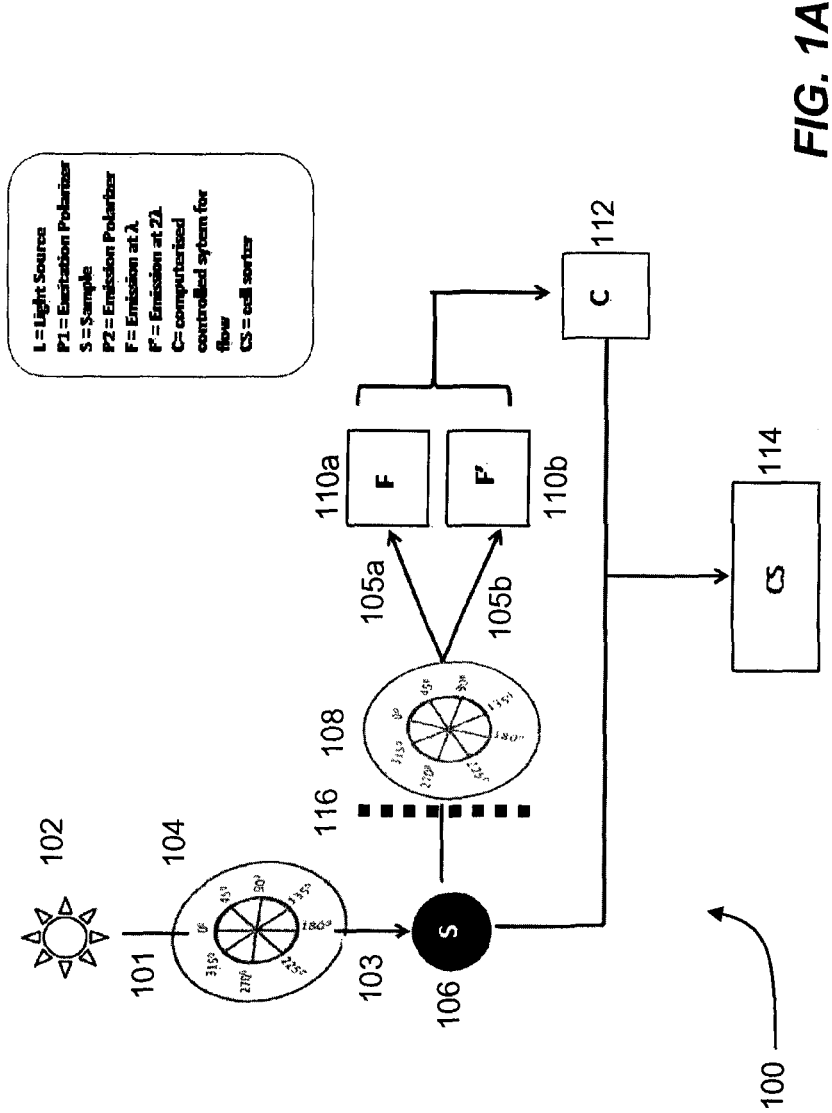
FIG. 1A is a schematic diagram of a flow cytometry system configured to determine a nonlinear optical property (e.g., anisotropy or chirality) of a sample based on its half-frequency emission.

FIG. 1A illustrates an instrument 100 (for example, a QuantaMaster™ fluorescence spectrometer made by Photon Technology International, Binghampton, N.J.) configured to make full- and half-frequency emission spectrum measurements. The instrument 100 includes a light source 102, such as a tunable laser or a broadband source with a tunable filter that emits a beam 101 of light at the excitation wavelength.

The emitted beam 101 propagates through a first polarizer 104, which can be rotated through a first series of angles (for example, 0°, 15°, 30°, 45°, 60°, 75°, 90°, and any angle between 0° and 90°). The first polarizer 104 transforms the emitted beam 101 into a polarized beam 103 with a linear polarization state whose orientation equals the rotation angle of the polarizer 104. The flow cytometer may optionally include a quarter-wave retarder disposed after the first polarizer 104 to transform the linearly polarized beam 103 into an elliptically or circularly polarized beam. The polarized beam 103 illuminates a sample 106, which may include fluorescent material, including but not limited to fluorescent cells, fluorescent particles, cells marked with fluorescent tags, or other particles/molecules marked with fluorescent tags. The sample 106 may be suspended in fluid flowing into, through, or out of a flow cytometer.

Without subscribing to or being bound by any particular theory, experimental data suggest that the fluorescent material in the sample 106 emits light at both a full-frequency emission wavelength 105a and a half-frequency emission wavelength 105b when illuminated by the linearly polarized beam of light 103. A grating 116 (shown here as a transmission grating; other embodiments may use reflection gratings) diffracts the emitted light 105a, 105b at different angles as well understood by those of skill in the art. If desired, the instrument 100 may include a dichroic filter, prism, or other device to further separate the half-frequency emission 105b from the full-frequency emission 105a. The diffracted light 105a, 105b propagates through a second polarizer 108 that can be rotated through a second series of angles (e.g., 0°, 15°, 30°, 45°, 60°, 75°, 90°, and any angle between 0° and 90°).

The instrument 100 includes a pair of detectors 110a, 110b that detect the full- and half-frequency diffracted beams 105a, 105b in parallel. The full-frequency diffracted beam 105a illuminates the first detector 110a, which emits a photocurrent whose amplitude varies with the amplitude of the detected portion of the full-frequency diffracted beam 105a. Similarly, the half-frequency diffracted beam 105b illuminates the second detector 110b, which emits a photocurrent whose amplitude varies with the amplitude of the detected portion of the half-frequency diffracted beam 105b. If desired, the detectors 110a, 110b may be selected, optimized, or filtered to detect radiation only in a specific subband, i.e., a subband centered about the full frequency or a subband centered about the half frequency.

A controller 112 coupled to the detectors 110a, 110b senses and records representations of the photocurrents from the detectors 110a, 110b. The controller 112 also determines the type of fluorescent material (for example, the type of fluorescent particle or tag) in the sample 106 based on a ratio of the signals from the detectors 110a, 110b, as described below, and actuates a cell sorter 114 based on its determination. In one example, the cell sorter 114 is implemented as a programmable valve that opens (or closes) in response to full- and half-frequency signals indicating the presence (or absence) of a particular type of cell. The cell sorter 114 may actuate the flow cytometer so as to direct the flowing fluid containing or comprising the sample 106 into a particular channel or path.

In operation, the instrument 100 is programmed to detect emission at the fundamental emission subband as well as emission occurring at a subband centered about twice the wavelength at which the normal maxima is observed—i.e., the half-frequency portion of the spectrum. Exemplary subbands may be 1 nm, 5 nm, 10 nm, 15 nm, 20 nm, or 25 nm wide. The instrument 100 is also programmed to detect anisotropy at the full-frequency subband as well as at the half-frequency subband. The first and second polarizers 104 and 108 are set to first and second polarization angles, e.g., 0° and 15°, respectively, and the light source 102 is turned on to illuminate the sample 106. Once the detectors 110a, 110b have measured forward-scattered and 90°—scattered light at the first pair of polarization angles, the polarization angles are changed (e.g., to 0° and 30°, respectively), and the measurements are repeated. Full- and half-frequency measurements may be repeated for every possible combination of polarization angles or as desired to provide a measurement of the sample's nonlinear optical properties.

Figure 1B:
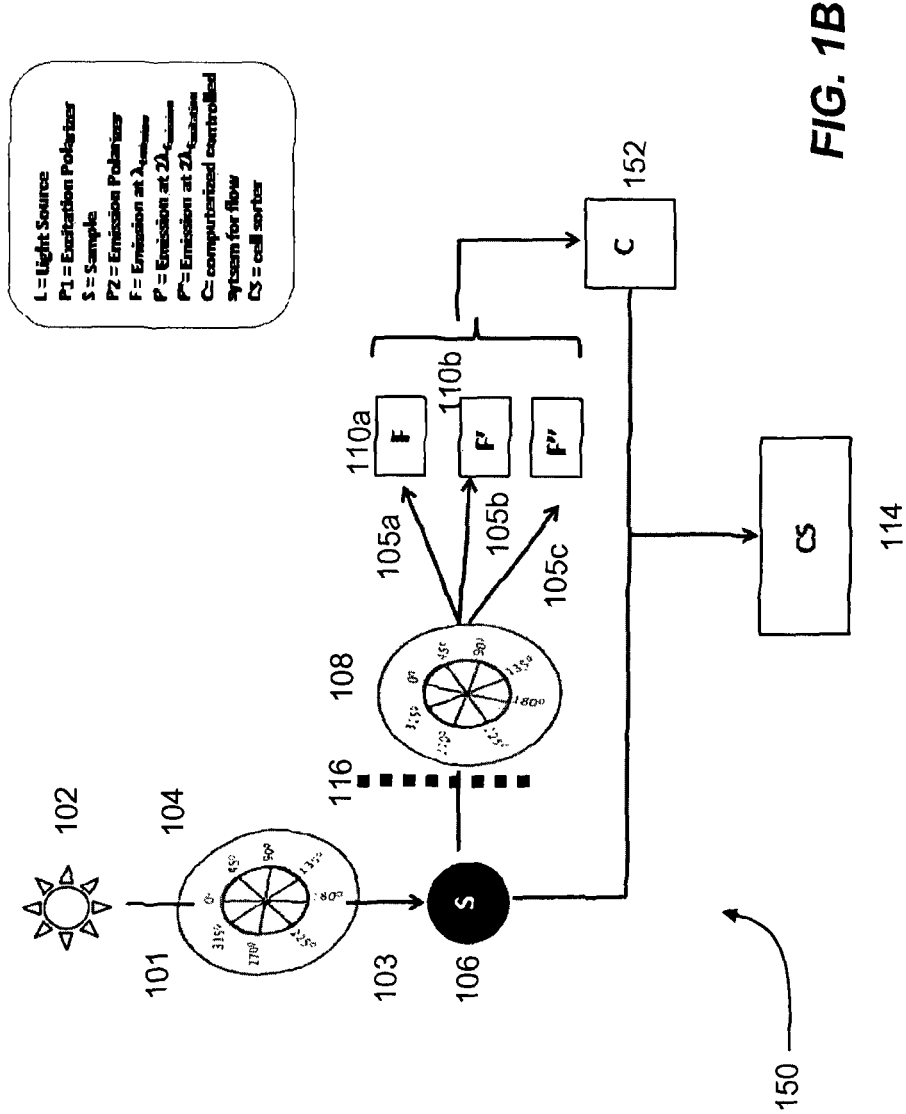
FIG. 1B is a schematic diagram of a flow cytometry system configured to determine a nonlinear optical property (e.g., anisotropy or chirality) of a sample based on its half-frequency emission and the half-frequency excitation.

FIG. 1B is a schematic diagram of an instrument 150 configured to make full- and half-frequency emission spectrum measurements as well as measurements of the half-frequency excitation spectrum. Like the instrument 100 shown in FIG. 1A, the instrument 150 includes a light source 102, such as a tunable laser or a broadband source with a tunable filter that emits a beam 101 of light at the excitation wavelength. The emitted beam 101 propagates through a first polarizer 104, which can be rotated through a first series of angles (for example, 0°, 15°, 30°, 45°, 60°, 75°, 90°, and any angle between 0° and 90°). The first polarizer 104 transforms the emitted beam 101 into a polarized beam 103 with a linear polarization state whose orientation equals the rotation angle of the polarizer 104. The flow cytometer may optionally include a quarter-wave retarder disposed after the first polarizer 104 to transform the linearly polarized beam 103 into an elliptically or circularly polarized beam. The polarized beam 103 illuminates a sample 106, which may include fluorescent material, including but not limited to fluorescent cells, fluorescent particles, cells marked with fluorescent tags, or other particles/molecules marked with fluorescent tags. The sample 106 may be suspended in fluid flowing into, through, or out of a flow cytometer.

A grating 116 (shown here as a transmission grating; other embodiments may use reflection gratings) diffracts light 105a and 105b emitted by the sample at angle proportional to the wavelength as described above. The grating 116 also diffracts light 105c at the half frequency of the excitation spectrum, i.e., the spectrum of the light 103 that excites the sample 106. The diffracted light 105a, 105b, and 105c passes through a second polarizer 108 that can be rotated through a second series of angles (e.g., 0°, 15°, 30°, 45°, 60°, 75°, 90°, and any angle between 0° and 90°), then illuminates respective detectors 110a, 110b, and 110c, which emit respective photocurrents whose amplitudes vary in proportion to the detected intensity. A controller 152 coupled to the detectors 110a, 110b, and 110c senses and records representations of the photocurrents from the detectors 110a, 110b, and 110c. The controller 152 also determines the type of fluorescent material (for example, the type of fluorescent particle or tag) in the sample 106 based on a ratio of the signals from the detectors 110a, 110b, and 110c, as described below, and actuates a cell sorter 114 based on its determination. The cell sorter 114 may actuate the flow cytometer so as to direct the flowing fluid containing or comprising the sample 106 into a particular channel or path.

Those of skill in the art will readily appreciate that other instrument architectures are also possible and fall within the scope of the claimed subject matter. For instance, an alternative instrument may include a single detector array, such as a charge-coupled device (CCD) or complementary metal-oxide-semiconductor (CMOS) array, instead of separate detectors to detect fluorescent emission at both the full and half frequencies. Alternatively, an instrument may include a rotating grating that scans the full- and half-frequency beams across a single detector in a sequential fashion or a dichroic filter that flips into and out of position before a single detector that detects the full- and half-frequency beams in sequential fashion. In other embodiments, one or more detectors may be positioned to detect light that is scattered or emitted at different angles from the sample 108. For example, an instrument may detect both forward-scattered light (i.e., light at an angle of 0° with respect to the propagation angle of the polarized beam 103) and light scattered at a 90° angle with respect to the propagation angle of the polarized beam 103, e.g., using reconfigurable mirrors (flip mirrors) to route light to the detectors from different angles.

Figure 1C:
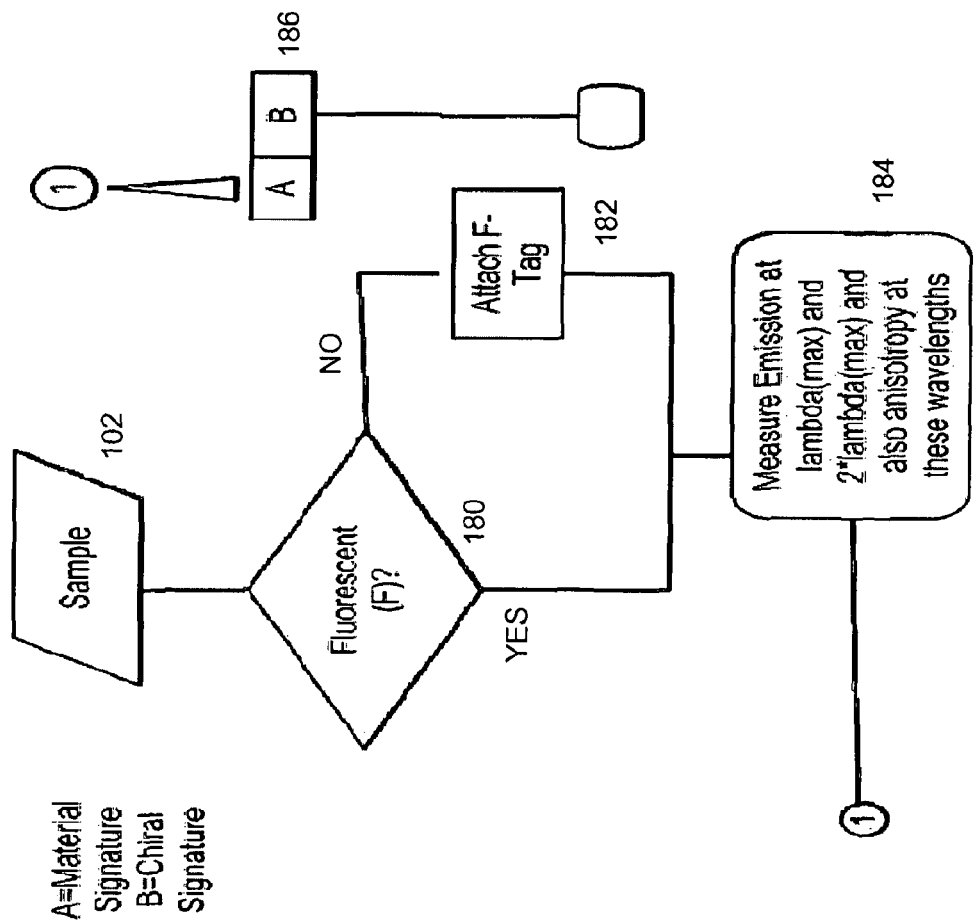
FIG. 1C is a flow diagram that illustrates operation of the instruments of FIGS. 1A and 1B.

FIG. 1C is a flow diagram that illustrates how to measure a nonlinear optical property (e.g., anisotropy, chirality, or both) using the instruments 100 (FIG. 1A) and 150 (FIG. 1B). In block 180, the user determines whether or not the sample 102 is fluorescent. If the sample is not fluorescent, the user attaches one or more fluorescent tags to the sample 102 in block 182. The user then proceeds to measure the intensity and anisotropy in the full-frequency and half-frequency emission bands in block 184 using the instrument 100, 150. The instrument 100, 150, a fluorometer, or another separate processor determines the material signature A and the chiral signature in block 186 to estimate or calculate a nonlinear optical property value (e.g., anisotropy value) for the sample 102.

Figure 1D:
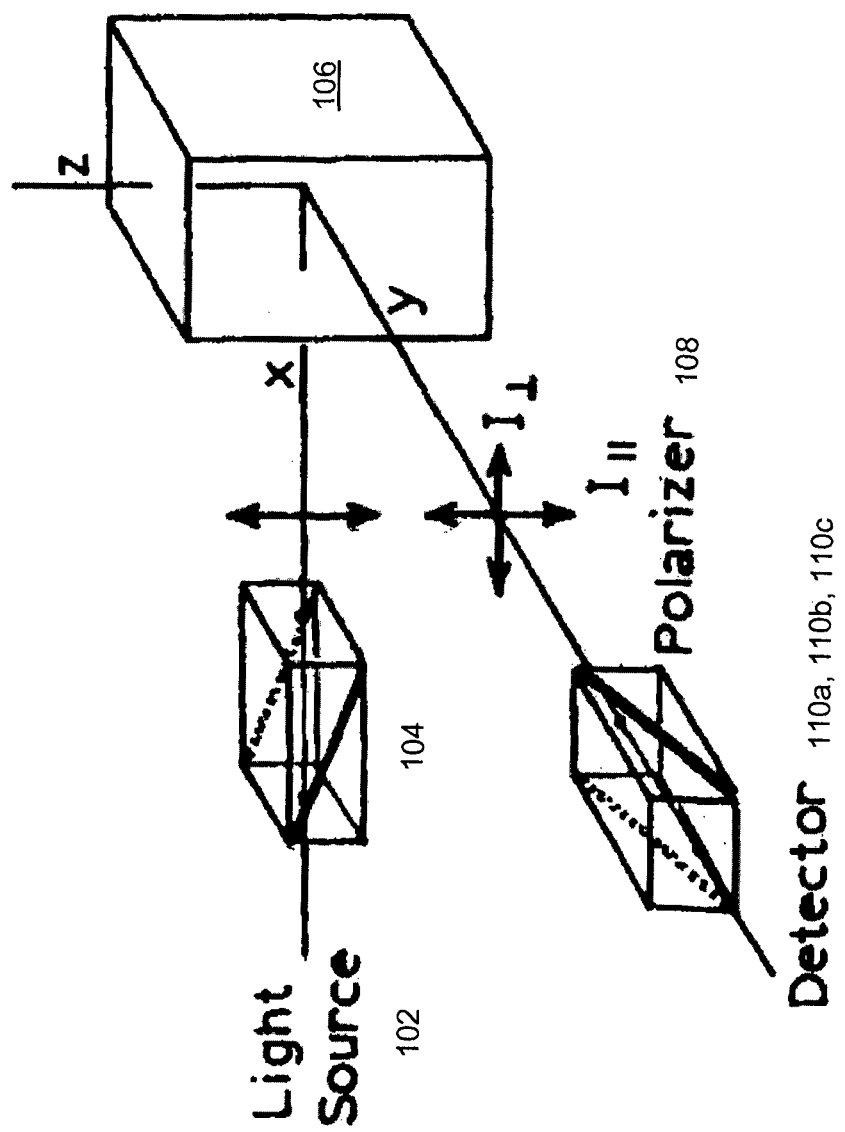
FIG. 1D is a schematic diagram illustrating a fluorescence anisotropy measurement.

FIG. 1D illustrates a nonlinear optical property (e.g., anisotropy, chirality, or both) measurement made using the components of FIG. 1A. For an anisotropy measurement, the sample 106 may be excited with vertically polarized light for the source 102 and first polarizer 104 and the intensity of the emission may be measured with the second polarizer 108 set parallel (II) with respect to the first polarizer 104 (termed as $I_{II}$). Similarly, when the emission is measured perpendicular ($\perp$) with respect to excitation emission, the intensity is termed as $I\perp$. Hence, mathematically anisotropy may be represented as $A=(I_{II}-I\perp)/(I_{II}+2I\perp)$. Alternatively, anisotropy can also defined as $A=[I_{VV}-G*I_{VH}]/[I_{VV}+2G*I_{VH}]$ to minimize the error occurred due to polarizer or instrument, where $I_{12}$ indicates the intensity measured with the first polarizer 104 set to angle 1 and the second polarizer 108 set to angle 2, V indicates a vertical polarization state, H indicates a horizontal polarization state, and $G=I_{HV}/I_{HH}$ is a constant that represents the ratio of the sensitivities of the detection system for vertically and horizontally polarized light.

The polarization states of the incident and emitted beams reveal information about the anisotropy and/or chirality of the particles in the sample. If $(\theta, \Phi)$ represent the polarization angles of the first (excitation) polarizer 104 and second (emission) polarizer 108, respectively, keeping the polarization angles at $(\theta, \theta)$ as a function of $\theta$ serves as a calibration of the polarizers. (In other words, the system may be calibrated with the excitation polarizer and emission polarizer rotated to the same angle, e.g., zero degrees.) Polarizer angle combinations such as $(\theta, \theta+\pi/2)$ reveal canonical information (i.e., independent information regarding different variables at the same time) about the particles being illuminated. Other combinations where $\theta \neq \Phi$ is also possible and reveal important shape information. One may have a mapping on the basis of $\theta-\Phi$. For each such combination, $I_\lambda$ and $I_{2\lambda}$ may be defined, where $I_\lambda$ and $I_{2\lambda}$ are emission intensity at emission maxima and its half frequency.

Distinguishing Chiral Molecules

Figure 2:
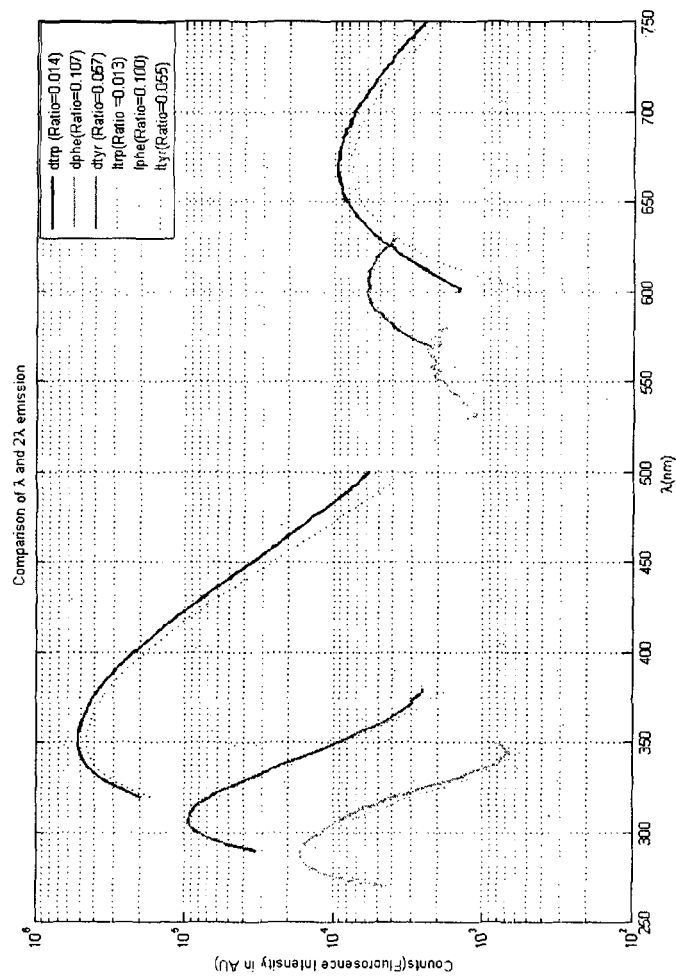
FIG. 2 is a plot of emission spectra with peaks at the fundamental frequency (left) and half frequency (right) for tryptophan, tyrosine, and phenylalanine obtained using the flow cytometry system of FIG. 1A.

FIG. 2 is a plot of emission spectra for samples of three different fluorescent chiral amino acids—in this case, tyrosine, tryptophan and phenylalanine—acquired using the instrument 100 depicted in FIG. 1A. Each sample included two different forms of a single amino acid: a dextrotatory (D) form that rotates linearly polarized light in a clockwise fashion (when viewed facing the light source) and a levorotary (L) form that rotates linearly polarized light in a counterclockwise fashion (when viewed facing the light source). The plot was obtained by exciting each sample with 0°-polarized beam at its respective excitation wavelength, $\lambda_{ex}$, and measuring the 0°-polarized emission at each sample's respective fundamental emission wavelength, $\lambda_1$, and respective half-frequency emission wavelength, $\lambda_2=2\lambda_1$. (TABLE 1 shows the excitation wavelength, full-frequency emission wavelength, and half-frequency emission wavelength for each of several amino acids, including tyrosine, tryptophan and phenylalanine.) Each spectrum has peaks in at both the fundamental frequency and the half frequency.

A user or the controller 112 can determine a nonlinear optical property, such as anisotropy or chirality, of the sample by taking the ratio of the areas under the full- and half-frequency peaks or the ratio of the amplitudes of the full- and half-frequency peaks. These ratios can be compared to ratios stored in a database for chiral vectors generated from full frequency and half frequency signals. For instance, the controller 112 (or a separate processor) or a fluorometer may integrate the area under each peak using any suitable numerical integration technique, then divide the areas to yield the ratio, which can be interpreted as an extent of the fluorophore's nonlinear emission response. Similarly, the controller 112 (or a separate processor) may determine the heights of the full- and half-frequency peaks using a curve-fitting algorithm, Newton's Method, or any other suitable peak-finding technique, then divide the amplitudes to yield the ratio. Either of these ratios can be compared to a library of previously compiled ratios to identify the sample.

In the case of chiral molecules with different mirror image forms, the controller 112, fluorometer, or other processor may implement the following routine (pseudocode) to determine the areas under the peaks in FIG. 2:

```
www=[ ];
lem=[288 350 308];
lex=[257 280 274];
for i=1:3;% We have used three chiral molecules
ww=[ ];
sd=f{i};sl=f{i+3};
lam=sd.Sheet1(:,1);F=sd.Sheet1(:,2);
for w=5:15
[a 1l,a2l,a3l]=intarea(lam,Fl,lex(i),lem(i),w);
[a1d,a2d,a3d]=intarea(lam,Fd,lex(i),lem(i),w);
ww=[ww;[a1l/a1d a2l/a2d a3l/a3d]]
end
www{i}=ww;
end
```

Each sample was also subjected to an anisotropy measurement at both emission wavelengths $(\lambda_1, \lambda_2)$ as described above. A typical anisotropy measurement of a given sample takes approximately 15-20 minutes, although looking at a fixed emission wavelength may reduce the measurement time by an order of magnitude. Comparing the anisotropy measurements at the fundamental emission wavelength, $\lambda_1$, and the half-frequency emission wavelength, $\lambda_2$, shows that the anisotropic measurements at the half-frequency emission wavelength, $\lambda_2$, provide better discriminatory power between the D and L forms of each amino acid. As explained below, the enantiomeric dependence becomes more enhanced by comparing the anisotropies of the respective amino acids.

Figure 3:
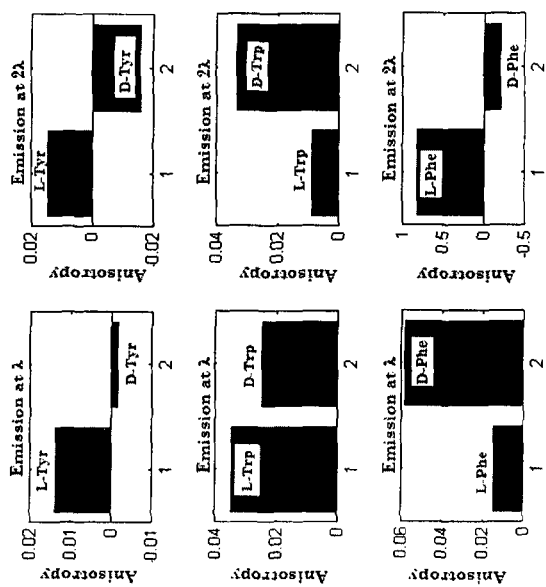
FIG. 3 shows anisotropy bar diagrams derived from the emission spectra plotted in FIG. 2 for different enantiomeric forms of tyrosine (top), tryptophan (middle), and phenylalanine (bottom).

FIG. 3 is a bar diagram showing the dimensionless anisotropy for L and D forms of different amino acids (both L and D) at their emission wavelength at their respective fundamental emission wavelengths, $\lambda_1$, and half-frequency emission wavelengths, $\lambda_2$. The upper left panel shows the anisotropy at $\lambda_1$ for L and D tyrosine, whereas the upper right panel shows the anisotropy at $\lambda_2=2\lambda_1$, for L and D tyrosine. The middle left ($\lambda_1$) and right ($\lambda_2=2\lambda_1$) panels show the anisotropy for L and D tryptophan, and the lower left ($\lambda_1$) and right ($\lambda_2=2\lambda_1$) panel illustrate the same parameter for L and D phenylalanine. (In general, achiral molecules tend to have low anisotropy values.)

Figure 4:
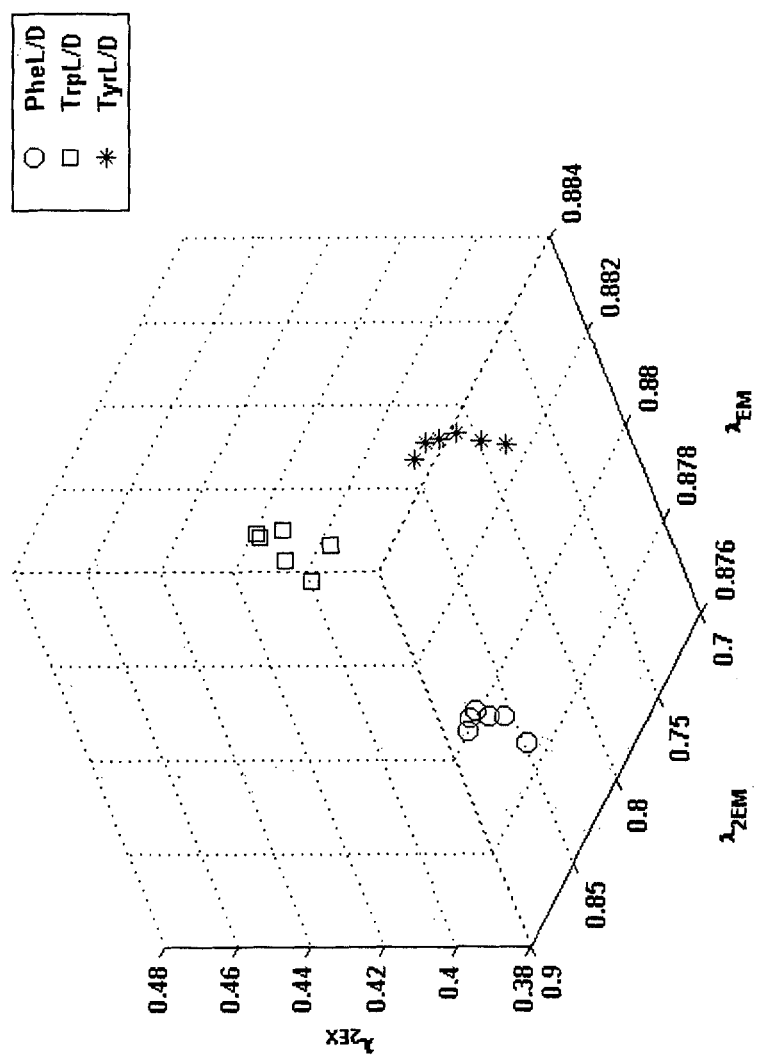
FIG. 4 is a three-dimensional scatter plot of intensity at the half-frequency excitation wavelength ($\lambda_{2EX}$) versus intensity at the emission wavelength ($\lambda_{EM}$) and the half-frequency emission wavelength ($\lambda_{2EM}$) for tyrosine (stars), tryptophan (squares) and phenylalanine (circles).

FIG. 4 is a three-dimensional scatter plot derived using the data from FIG. 2. The controller 112 (or fluorometer or other processor) may generate FIG. 4 using the following script:

```
sss={ };ss=[ ];
lamem=[700 788 ];
 lamem·[350 394];
 fw={fnamew_trp;fnamet};
for j=1:length(fname)
    [ex,em,qqq,rrr,lam,aa]=ptianal_aniso_norm(fname{j},lamem(j));
    [ex1,em1,qqq1,rrr1,lam1,bb]=ptianal_aniso_norm(fw{j},lamem(j));
    count=0;
for i=1:9
        count=count+1;
        subplot(3,3,count)
          s=rrr(:,i) -rrr1(:,i);
          ss=[ss s];
        maxs=max(s);
        mins=min(s);
        s=(s-mins)./(maxs-mins);
        %ss=[ss s];
        plot(em,s)
        title(['em=' num2str(em(i)) '^o'])
        xlabel(['em in ^o'])
        ylabel('Intensity')
          %axis{[0 400 0 1.5])
end
sss{j}=ss;
clear ss
ss=[ ];
    % subplot(4,2,i)
      figure
end
function [ex,em,qqq,rrr,lam,A]=ptianal_aniso_norm(fname,lamex);
[a,b]=xlsread(fname);
lam=a(:,1);
T=1:81;
ex=[0 45 90 135 180 225 270 315 360];
em=ex;
qqq(9,9)=0;
rrr(9,9)=0;
[r,c]=size(a);
 T=T(1:c/2);
A=a(1:r,2:c);
qq=[ ];rr=[ ];
for i=1:c/2
    ik=find(lam==lamex);
    qq=[qq;lam(ik)];
    rr=[rr;A(ik,i)];
end
count=0;
for i=1:9;
    for j=1:9
        count=count+1;
        qqq(i,j)=qq(count);
        rrr(i,j)=rr(count);
    end
end
count=0;
for i=1:9
        count=count+1;
        subplot(3,3,count)
        plot(em,rrr(:,i))
        title(['em=' num2str(em(i)) '^o'])
        xlabel(['em in ^o'])
        ylabel('Intensity')
        %axis([0 400 0 1.5])
end
```

The full frequency measurements and half frequency measurements plotted in FIGS. 3 and 4 show the anisotropy of both the L and D forms of each sample. However, the difference in anisotropy measurements for the L and D forms is greater for the half-frequency measurements than for the full-frequency measurements, which suggests that half frequency is a stronger discriminator of chirality. (Conventionally, anisotropy is not used to determine chirality.) Thus the difference of anisotropy between L and D forms is more conspicuous for half-frequency measurements than for full-frequency measurements.

FIGS. 5A and 5B show full-frequency emission patterns for achiral pyrene and chiral L-tryptophan, respectively. FIGS. 6A and 6B show half-frequency emission patterns for achiral pyrene and chiral L-tryptophan, respectively. These figures illustrate that the chiral and achiral signatures are reflected in both the full-frequency and half-frequency domains. The half-frequency based chirality data presented in FIGS. 6A and 6B is consistent with the full-frequency based discrimination disclosed in PCT/IB2011/001409, which is incorporated herein by reference in its entirety.

Distinguishing Achiral Molecules

As stated above, the half-frequency spectral signature provides a general discriminatory signature for both chiral and achiral material as the principle is based on nonlinear optical properties when one has differential emission of polarized light at a given resonant frequency and at half of the same frequency. For an achiral molecule, the expression for the extended asymmetry factor (as defined in PCT/IB2011/001409) may be a flat line without any variation with respect to polarization angle. Although achiral molecules, such as pyrene, may follow this pattern, the half-frequency spectral signature may be different in each achiral molecule, even though they are achiral.

Figure 7:
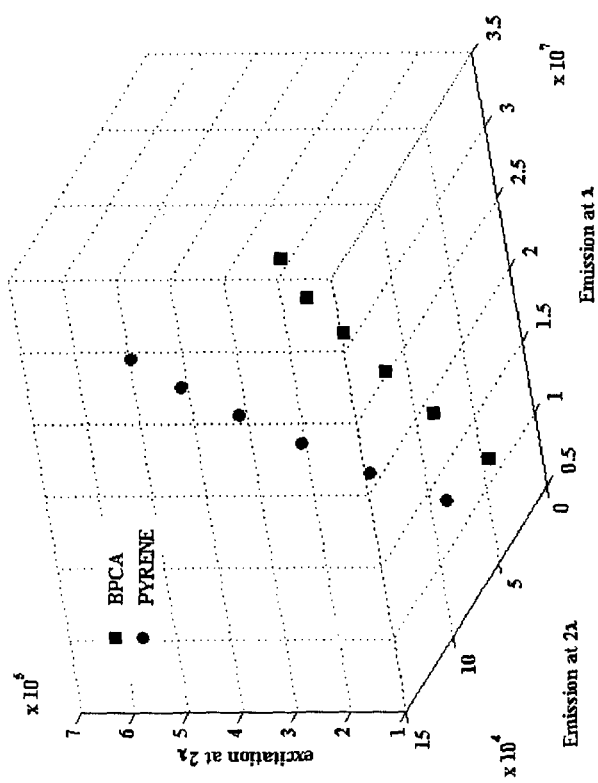
FIG. 7 is a three-dimensional scatter plot of intensity at the that illustrates discrimination of achiral 4-biphenyl carboxylic acid (BPCA) (squares) and achiral pyrene (circles) using integrated spectral intensities at different spectral bandwidths.

FIG. 7 is a three-dimensional scatter plot of intensity at the that illustrates discrimination of achiral 4-biphenyl carboxylic acid (BPCA) (squares) and achiral pyrene (circles) using integrated spectral intensities at different spectral bandwidths. This plot was generated by a processor that executed the following exemplary script on nonlinear optical property measurements (e.g., as described above) of BPCA and pyrene:

```
% Molecular Discrimination (independent of chiral content)
% The row contains a given emission wavelength intensity at lambda at
% different polarization angles
% Columns represnt response of fluor. intensity at lambda two lambda and
% also at double excitation wavelength
lem=input('Enter emission wavelengths for the molecule')
% if there are n molecules this should be input as [em1 em2 em3 ... emn]
lex=input('Enter excitation wavelengths for the molecule')
% if there are n molecules this should be input as [ex1 ex2 ex3 ... exn]
% EXAMPLE
% For PYRENE and BPCA
```

-continued

```
% lem=[394 396 ];
% lex=[ 334 312];
for i=1:length(z);
ww=[ ];
sd=f{i};
lam=sd.Sheet1(:,1);F=sd.Sheet1(:,2)
for w=5:.1:20
[a1l,a2l,a3l]=intarea(lam,F,lex(i),lem(i),w);
ww=[ww;[a1l a2l a3l]]
end
www{i}=ww;
end
for i=1:length (z)
     plot3(www{i}(:,1),www{i}(:,2),www{i}(:,3),'c')
     if i==1;hold ;end
end
function[a1,a2,a3]=intarea(lam,F,lex, lem,w)
% lamx1 =350 for trp , 308 for tyr & 288nm for phe
i1=find(lam<lem+w & lam>lem-w);
i2=find(lam<2*lem+w & lam>2*lem-w);
i3=find(lam<2*lex+w & lam>2*lex-w);
lam1=lam(i1);lam2=lam(i2);lam3=lam(i3);f1=F(i1);f2=F(i2);f3=F(i3);
a1=trapz(lam1,f1);a2=trapz(lam2,f2);a3=trapz(lam3,f3);
```

Racemic Mixtures

Figure 8A:
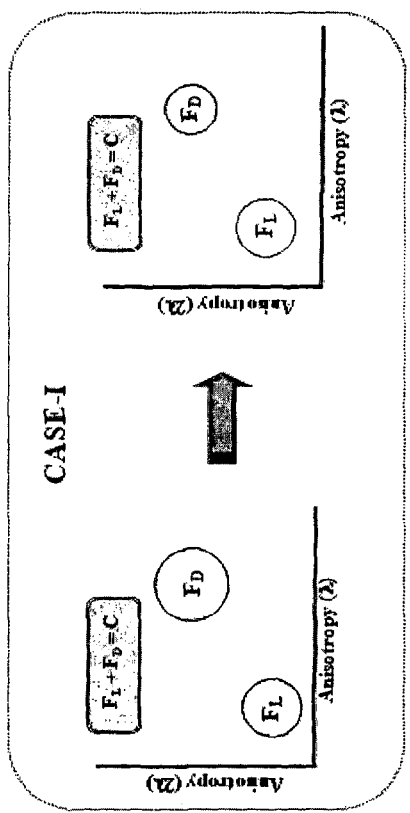
FIGS. 8A and 8B illustrate different cases for detection of racemic mixtures of enantiomers.
Figure 8B:
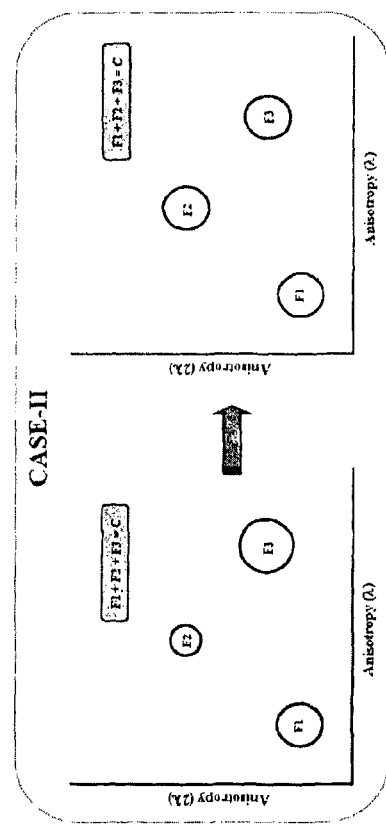

FIGS. 8A and 8B show phase diagrams that illustrate a how the half-frequency approach can be exploited in analyzing the mixture of enantiomers/fluorophores in a flow cytometry platform. Consider Case I, shown in FIG. 8A, in which F is a fluorophore having D and L enantiomeric forms denoted by $F_D$ and $F_L$, respectively, represented by circles of different diameters. Enantiomeric forms $F_D$ and $F_L$ are mixed together to form a hypothetical racemization in which the ratio of $F_D$ to $F_L$ (given by the ratio of the diameters) changes but the sum of $F_D$ and $F_L$ is constant. Comparing the phase diagram in the left panel of FIG. 8A to the phase diagram in the right panel of FIG. 8A shows that the ratio of $F_D$ to $F_L$ changes, as indicated by the change in circle diameters. Similarly, in Case II, shown in FIG. 8B, $F_1$, $F_2$, and $F_3$ are three different fluorophores in a given mixture of protein. The proportions of the fluorophores vary but their cumulative mole fraction stays constant. In both Case I and Case II, the different enantiomeric forms or fluorophores can be separated by measuring the anisotropy at both $\lambda_1$ and $\lambda_2=2\lambda_1$, then directing the different enantiomeric forms or fluorophores into different channels or chambers using the instrument 100 of FIG. 1A.

Example 1: Half-Frequency Spectral Signature Measurements

TABLE 1 shows the excitation wavelength, full-frequency emission wavelength, and half-frequency emission wavelength for a different chiral and achiral samples.

TABLE 1

| Sample | Excitation Wavelength | Full-Frequency Emission Wavelength ($\lambda_1$) | Half-Frequency Emission Wavelength ($\lambda_2$) |
|---|---|---|---|
| Tryptophan | 280 nm | 350 nm | 700 nm |
| Tyrosine | 274 nm | 308 nm | 616 nm |
| Phenylalanine | 257 nm | 288 nm | 567 nm |
| Fluorescent achiral pyrene molecule | 334 nm | 394 nm | 788 nm |

Example 2: Sorting Racemic Mixtures

A lab produces a fluorescent compound in L and D enantiomeric forms. The L form exhibits pharmaceutical properties, but the D form is inert in small doses (and may even be toxic at higher doses). Unfortunately, synthesis yields a racemic mixture of the compound. A flow cytometer coupled to a cell sorter separates the racemic mixture by first identifying each enantiometer from its half-frequency spectral signature. As described above, the flow cytometer illuminates a portion of the racemic mixture with polarized light at an excitation wavelength. The excitation illumination causes the enantiomers to fluoresce. A grating diffracts the light emitted by the enantiomers towards a pair of polarizing detectors that sense the amplitudes of the diffracted light at the full emission frequency and the half emission frequency. The system takes the ratio of the signal amplitudes at the full and half emission frequencies, then determines whether the particle is an L or D enantiometer based on the ratio. An actuating valve shunts L enantiomers into a first channel and D enantiomers into a second channel.

Example 3: Half-Frequency Microscopy

A fluorescence microscope includes a light source that illuminates a sample with light at an excitation wavelength. The sample emits light at both a fundamental frequency and a half frequency. A dichroic beamsplitter transmits the light at the fundamental frequency through a first objective, which images the transmitted light onto a first two-dimensional detector array (e.g., a CCD or CMOS array). The dichroic beamsplitter reflects the light at the half frequency through a second objective, which images the reflected light onto a second two-dimensional detector array. The two images can be processed separately, overlaid, or otherwise processed to provide an indication of how the anisotropy varies over the image region of the sample.

Example 4: Identifying Fluorescent Tags for Bioimaging

Embodiments of the present technology can be used to search for probes (e.g., fluorescent tags) appropriate for use in bioimaging. It may be interesting to examine whether one can use the same probe beyond the domain of its conventional application. Development of such methodology may be beneficial to end users in economic terms, and more versatile use of any bioimaging facility.

The subject matter disclosed herein sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

We claim:

1. A method of determining a nonlinear optical property of a fluorescent material, the method comprising:
   irradiating the fluorescent material at an excitation frequency;
   detecting a fluorescence spectrum of the fluorescent material, wherein the fluorescence spectrum includes a first fluorescence peak at a first frequency and a second fluorescence peak at a second frequency equal to about half the first frequency;
   performing a comparison of the first fluorescence peak to the second fluorescence peak;
   determining the nonlinear optical property of the fluorescent material based on the comparison, wherein the nonlinear optical property of the fluorescent material includes an anisotropy associated with the fluorescent material; and
   sorting the fluorescent material based on the nonlinear optical property of the fluorescent material.

2. The method of claim 1, wherein the nonlinear optical property of the fluorescent material further includes a chirality associated with the fluorescent material.

3. The method of claim 1, wherein the fluorescent material includes a cell with a fluorescent tag.

4. The method of claim 1, wherein the fluorescent material is a molecule with a fluorescent tag.

5. The method of claim 1, wherein the fluorescent material includes a pharmaceutical compound.

6. The method of claim 1, wherein irradiating the fluorescent material further comprises selecting radiation at the excitation frequency in a first polarization state; and
   wherein detecting the fluorescence spectrum further comprises selecting radiation at the first frequency and the second frequency in a second polarization state.

7. The method of claim 6, wherein the first polarization state is orthogonal to the second polarization state.

8. The method of claim 6, further comprising:
   changing at least one of the first and second polarization states; and
   detecting another fluorescence spectrum.

9. The method of claim 1, wherein irradiating the fluorescent material further comprises irradiating the fluorescent material at a first angle and detecting the fluorescence spectrum further comprises detecting radiation at a second angle with respect to the fluorescent material.

10. The method of claim 9, wherein the first angle is different than the second angle.

11. The method of claim 9, wherein the first angle and the second angle are 90° apart.

12. The method of claim 1, wherein the excitation frequency is about 750 THz to about 30,000 THz.

13. The method of claim 1, wherein the excitation frequency is about 375 THz to about 750 THz.

14. The method of claim 1, wherein the excitation frequency is about 187.5 THz to about 375 THz.

15. The method of claim 1, wherein detecting the fluorescence spectrum further comprises:
   diffracting radiation emitted by the fluorescent material off a grating;
   filtering radiation at an excitation wavelength from the radiation emitted by the fluorescent material; and
   sensing the radiation emitted by the fluorescent material.

16. The method of claim 15, wherein sensing the radiation emitted by the fluorescent material includes detecting the radiation at the first frequency and the second frequency in parallel.

17. The method of claim 15, wherein sensing the radiation emitted by the fluorescent material includes detecting the radiation at the first frequency and the second frequency in series.

18. The method of claim 1, wherein the first frequency is about 375 THz to about 750 THz.

19. The method of claim 1, wherein the first frequency is about 187.5 THz to about 375 THz.

20. The method of claim 1, wherein performing the comparison of the first fluorescence peak to the second fluorescence peak comprises:
  estimating a first area under the first fluorescence peak;
  estimating a second area under the second fluorescence peak; and
  calculating a ratio of the first area to the second area.

21. The method of claim 1, wherein, if the fluorescent material is chiral, further comprising determining whether the fluorescent material has left-handed chirality or right-handed chirality based on a reference.

22. The method of claim 1, further comprising:
  determining whether the fluorescent material includes a monomer or a dimer based on the nonlinear optical property.

23. The method of claim 1, wherein the first frequency comprises a full-frequency wavelength and the second frequency comprises a half-frequency wavelength.

* * * * *

UNITED STATES PATENT AND TRADEMARK OFFICE
CERTIFICATE OF CORRECTION

| | | |
|---|---|---|
| PATENT NO. | : 9,897,543 B2 | Page 1 of 1 |
| APPLICATION NO. | : 14/364574 | |
| DATED | : February 20, 2018 | |
| INVENTOR(S) | : Dasgupta et al. | |

It is certified that error appears in the above-identified patent and that said Letters Patent is hereby corrected as shown below:

In the Specification

In Column 3, Line 1, delete "material off" and insert -- material of --, therefor.

In Column 4, Lines 1-2, delete "intensity at the that" and insert -- intensity that --, therefor.

In Column 7, Line 6, delete "sample 108." and insert -- sample 106. --, therefor.

In Column 7, Line 37, delete "I⊥ Hence," and insert -- I⊥. Hence, --, therefor.

In Column 10, Lines 45-46, delete "intensity at the that" and insert -- intensity that --, therefor.

In Column 12, Line 5, delete "enantiometer" and insert -- enantiomer --, therefor.

In Column 12, Line 15, delete "enantiometer" and insert -- enantiomer --, therefor.

In Column 13, Line 18, delete "recitation no" and insert -- recitation, no --, therefor.

In Column 13, Line 41, delete "general such" and insert -- general, such --, therefor.

In Column 13, Line 48, delete "general such" and insert -- general, such --, therefor.

In the Claims

In Column 14, Line 64, in Claim 15, delete "off a" and insert -- of a --, therefor.

Signed and Sealed this
Nineteenth Day of June, 2018

Andrei Iancu
*Director of the United States Patent and Trademark Office*